United States Patent [19]

Yasuda et al.

[11] 4,235,096

[45] Nov. 25, 1980

[54] GAS DETECTION APPARATUS

[75] Inventors: Eturo Yasuda; Yoshihiro Segawa, both of Okazaki; Minoru Ohta, Anjo, all of Japan

[73] Assignee: Nippon Soken, Inc., Nishio, Japan

[21] Appl. No.: 4,189

[22] Filed: Jan. 17, 1979

[30] Foreign Application Priority Data

Jan. 19, 1978 [JP] Japan .................................. 53-4867

[51] Int. Cl.³ ........................................... G01N 27/12
[52] U.S. Cl. ........................................ 73/23; 123/440
[58] Field of Search ............ 73/23, 27 R; 123/32 EE, 123/119 EC; 60/276, 285; 340/632, 634; 422/98

[56] References Cited

U.S. PATENT DOCUMENTS

| 3,959,765 | 5/1976 | Stewart | 338/34 |
| 4,147,513 | 4/1979 | Bienkowski et al. | 73/23 |

Primary Examiner—Stephen A. Kreitman
Attorney, Agent, or Firm—Cushman, Darby & Cushman

[57] ABSTRACT

A gas detection apparatus with a gas detection element of which the electric resistance changes in accordance with a gas constituent, especially oxygen, in exhaust gas, wherein a fixed voltage is applied to a series circuit of the gas detection element and the reference resistor, and from the voltge at the voltage dividing point between the gas detection element and the reference resistor it is detected whether the gas constituent has exceeded a predetermined range or not. The gas detection apparatus includes a plurality of comparators each for comparing the voltage at the voltage dividing point with a corresponding one of the reference voltages to generate a comparison signal, and a logic circuit responsive to the rise or fall of the comparison signals showing that the gas constituent has exceeded a predetermined range.

4 Claims, 5 Drawing Figures

GAS DETECTION APPARATUS

BACKGROUND OF THE INVENTION

This invention relates to a gas detection apparatus, e.g., an apparatus for detecting a gas constituent in the exhaust gas of an engine for the purpose of enhancing the rate of purification of a catalytic converter for purifying the exhaust gas.

Conventionally as an apparatus for detecting a gas constituent in the exhaust gas of an engine there has been proposed an apparatus which comprises a gas detecting element of a metal oxide semiconductor such as titanium oxide whose electric resistance depends on a relative gas constituent and a comparator which converts the resistance of the gas detection element to a voltage by connecting the element in series with a fixed reference voltage and compares the voltage with a reference voltage in order to give an output signal indicative of a gas constituent.

However, the above prior art apparatus has only one reference voltage for comparison and the reference voltage is fixed. Therefore, if the electric resistance of the gas detection element changes in accordance with the working temperature or with the lapse of time, an erroneous detection of gas constituents may occur or it may become impossible to make detection.

SUMMARY OF THE INVENTION

Therefore, in view of the above-mentioned problem, an object of this invention is to provide a gas detection apparatus capable of detecting gas constituents satisfactorily without being influenced by working temperatures and characteristic changes over the lapse of time.

A gas detecting apparatus according to this invention comprises a series circuit of a gas detection element and a fixed reference resistor, a plurality of reference voltage generators each generating different reference voltages respectively, and a plurality of comparators each for comparing the voltage at the connection point between the gas detection element and the fixed reference resistor with the corresponding reference voltage.

A set of adjacent ones of the reference voltages is set to provide upper and lower limits respectively within which the voltage of the connection point changes under normal change of a gas constituent when the resistance characteristic of the gas element is not influenced by the working temperature or changes over the lapse of time, and other sets of adjacent ones of said reference voltages are set to provide each upper and lower limits respectively within which the voltage of the connection point changes under normal change of a gas constituent when the resistance characteristic of the gas element is influenced by the working temperature or the change over the lapse of time. When the voltage at the connection point exceeds any one of the reference voltages either in increasing or decreasing manner, a signal is generated to indicate that the gas constituent has changed over a predetermined fixed value. Thus, even if the electric resistance of the gas detection element changes in response to the change of the working temperature or with the lapse of time, a proper detection of the gas constituent can be ensured.

BRIEF DESCRIPTION OF THE DRAWINGS

These and other objects and advantages of the present invention will become apparent by reference to the following description and accompanying drawings wherein.

DESCRIPTION OF THE PREFERRED EMBODIMENT

Figure 1:
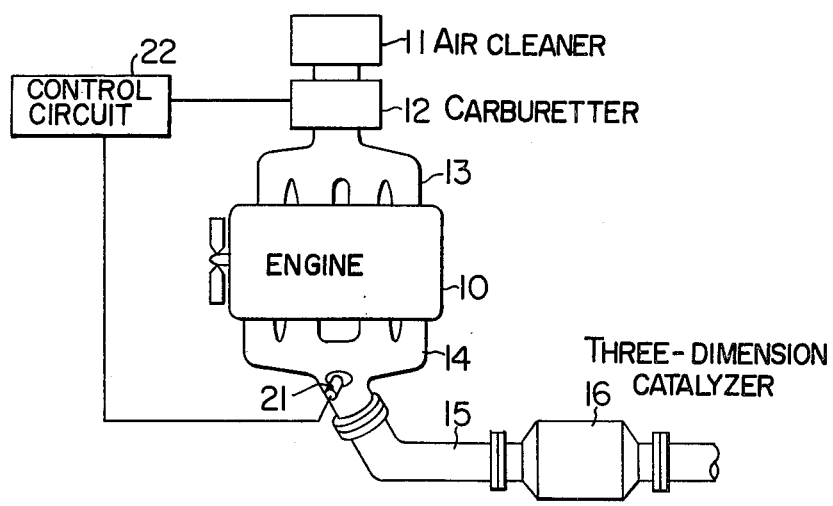
FIG. 1 shows a whole construction diagram of an embodiment of this invention.

In FIG. 1 there is shown a system to which this invention is applied. The engine 10 is a known spark ignition type engine, and the air intake system of the engine is composed of an air cleaner 11, a carburetor 12 and an air intake manifold 13, and the exhaust system of the engine is composed of an exhaust manifold 14, an exhaust pipe 15, a three-dimension catalytic converter 16 for cleaning the exhaust gas, and a muffler (not shown).

Here, the carburetor 12 has a known air-to-fuel ratio adjuster and in response to an electric signal the air-to-fuel ratio A/F of the gas mixture is changed. The three-dimension catalytic converter 16 efficiently purifies $NO_x$, HC, and CO simultaneously when the gas mixture whose air-to-fuel ratio is near a theoretical one is supplied to the engine. A known pellet type or honeycomb type catalyst is comprised in the converter 16.

Next, description will be made with respect to the gas detection means which is composed of a gas detection element 21 mounted on a collecting part of the exhaust manifold 14 and a control circuit 22 which supplies an electric signal to the carburetor 12.

Figure 2:
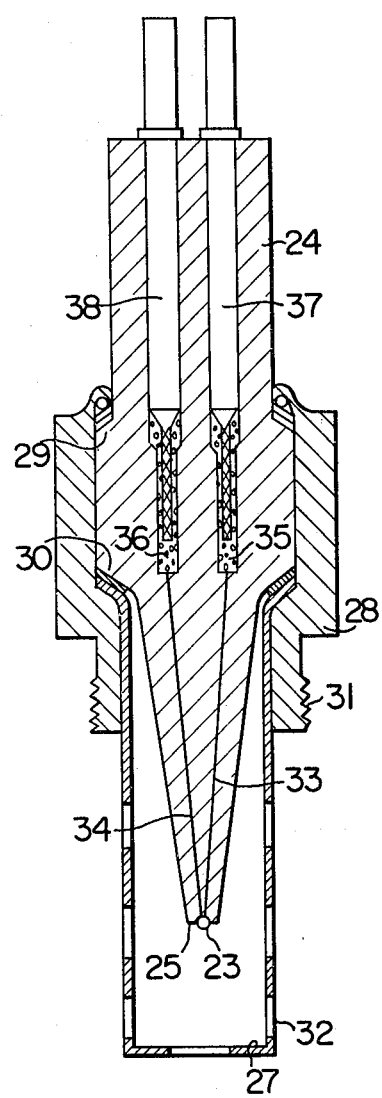
FIG. 2 shows a cross-sectional view of a gas detection element shown in FIG. 1.

The gas detection element 21 has a structure as shown in FIG. 2. In FIG. 2 a disk-type element piece 23 having an electric resistance which changes in response to the gas constituent in exhaust gas, specifically the oxygen concentration, is formed by a metal oxide semiconductor such as titanium oxide ($TiO_2$). On the surface of the disk-type piece 23, a catalyzer metal such as platinum (pt), Rhodium (Rh) etc. is attached. The piece 23 is mounted on a tip groove part 25 of a heat-proof and electrically insulated holder 24 of sintered material, e.g. alumina.

To the holder 24, a heat-proof metal protecting cover 27 and a housing 28 are coupled integrally or in one unit through an O-ring and a washer etc. at taper portions 29 and 30. The housing 28 is fixed to the exhaust manifold 14 through a screw portion 31.

The protecting cover 27 is provided to protect the element piece 23 from the exhaust gas flow and has a number of holes 32 through which the exhaust gas can pass.

Figure 3:
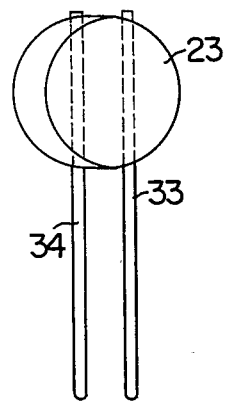
FIG. 3 shows an enlarged perspective view of a piece of gas detection element shown in FIG. 2.

Two platinum electrodes 33 and 34 are inserted into the element piece 23 to form an integrated mold, as shown in FIG. 3. Terminal bars 37 and 38 are electrically connected to the electrodes 33 and 34 through electrically conductive glass pieces 35 and 36. Thus, the electric resistance of the element piece 23 is derived through the terminal bars 37 and 38.

Figure 4:
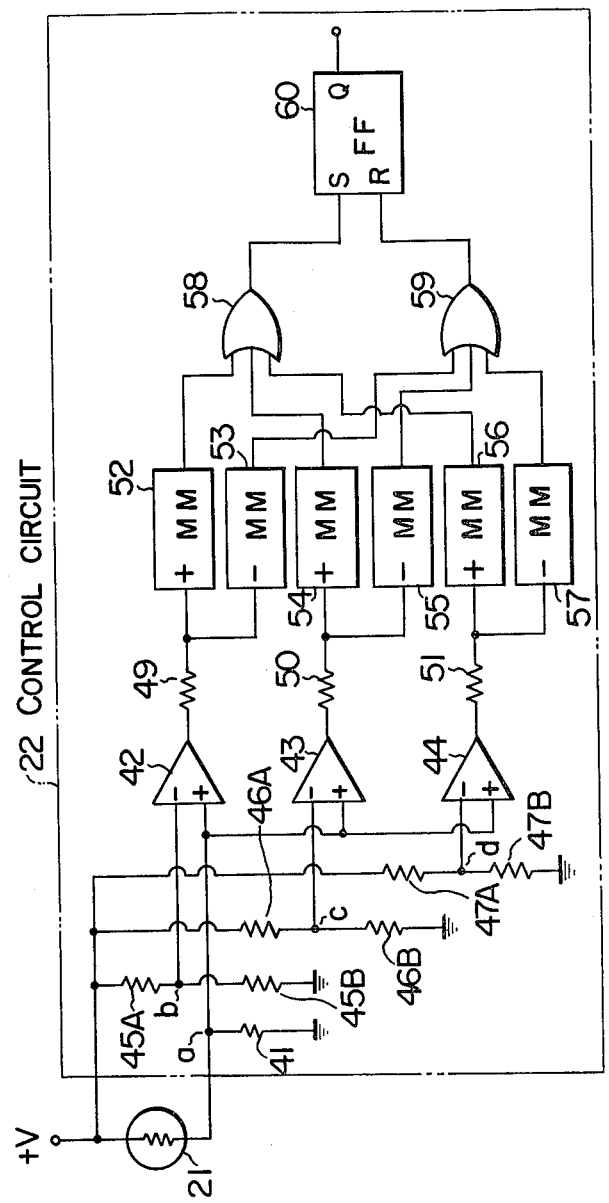
FIG. 4 shows an electric circuit diagram of a control circuit in the construction shown in FIG. 1.

Next, description will be made with respect to the control circuit 22 with reference to FIG. 4. In the control circuit 22 a reference resistor 41 is connected in series with the gas detection element 21 to which a d.c. voltage V is supplied. A potential dividing point a between the reference resistor 41 and the gas detecting element 21 is connected to non-inverting input terminals "+" of comparators 42, 43 and 44. Another potential dividing point b between dividing resistors 45A and 45B of a first reference voltage generator is connected to an inverting input terminal "−" of the comparator 42. A potential dividing point c between dividing resistors 46A and 46B forming a second reference voltage generator is connected to an inverting input terminal "−" of the comparator 43. A potential dividing point d between dividing resistors 47A and 47B forming a third reference voltage generator is connected to an inverting input terminal "−" of the comparator 44.

Here, assuming that the electric resistance of the reference resistor 41 is 300 k$\Omega$, it will be preferable to set the resistance values of resistors 45A and 45B to 900 and 300 k$\Omega$ respectively, those of resistors 46A and 46B each to 300 k$\Omega$, and those of resistors 47A and 47B to 100 k$\Omega$ and 300 k$\Omega$ respectively.

In this construction, the first reference voltage generator provides a reference voltage of $\frac{1}{4}$V to the comparator 42, the second reference voltage generator provides a reference voltage of $\frac{1}{2}$V to the comparator 43, and the third reference voltage generator provides a reference voltage of $\frac{3}{4}$V to the comparator 44.

Output terminals of the comparators 42, 43 and 44 are connected to monostable multivibrators 52, 53, 54, 55, 56 and 57 through protecting resistors 49, 50 and 51 respectively. The multivibrators are classified into two kinds. The monostable multivibrators 52, 54 and 56 are each triggered when the input signal rises from "0" to "1" level and generates one pulse signal, while the other monostable multivibrators 53, 55 and 57 are each triggered when the input signal falls from "1" to "0" level and generates one pulse signal.

Output terminals of the monostable multivibrators 52, 54 and 56 are connected to an input terminal of an OR gate 58, while output terminals of the monostable multivibrators 53, 55 and 57 are connected to an input terminal of an OR gate 59.

The output terminal of the OR gate 58 is connected to a set terminal S of a flip-flop 60 while the output terminal of the OR gate 59 is connected to a reset terminal R of the flip-flop 60. And the output terminal of the flip-flop 60 is connected to a driving circuit (not shown) which drives the air-to-filter ratio adjuster of carburetor 12.

Monostable multivibrators 52 to 57, OR gates 58 and 59 and the flip-flop 60 constitute a logic circuit which produces a gas detection signal in response to the rise and fall of the comparison signals of the comparators 42 to 44.

Figure 5:
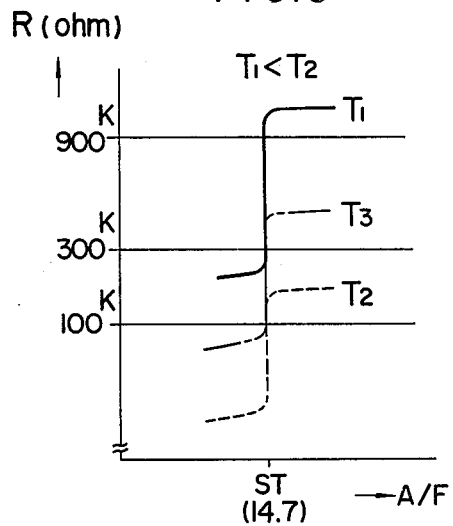
FIG. 5 shows a graph for the explanation of the operation of this invention.

In the above circuit construction, if the temperature of the exhaust gas is low so that the gas detecting element 21 is used at a working temperature $T_1$, the characteristic of air-to-fuel ratio A/F vs. the value of electric resistance R becomes as shown by a curve $T_1$ in FIG. 5.

Therefore, in this case, if the air-to-fuel ratio of the gas mixture formed in the carburetor 12 becomes larger than a set air-to-fuel ratio (theoretical ratio 14.7) ST, the constituent of the exhaust gas, specifically the oxygen concentration having a close relation to the air-to-fuel ratio varies and hence the resistance value of the gas detection element 21 becomes larger than the order of 1 M$\Omega$, that is, larger than the resistance of the dividing resistor 45A.

Therefore, the voltage at the point a is lower than the reference voltages at the points b, c and d, and each of the comparators generate a 0 level signal. Monostable multivibrators 53, 55 and 57 supply a reset signal to the reset terminal R through the OR gate 59, and the flip-flop 60 outputs a gas detection signal of "0" level.

As a result, it is judged that the air-to-fuel ratio is larger than the set value ST, and the air-to-fuel ratio adjuster of the carburetor 12 operates to decrease the air-to-fuel ratio, that is, to increase the concentration of the mixed gas.

On the other hand, if the air-to-fuel ratio of the gas mixture formed in the carburetor 12 becomes smaller than the set value ST at the working temperature $T_1$, the resistance value of the gas detection element 21 decreases to a value in the degree of 200 k$\Omega$.

Therefore, the voltage at the point a becomes larger than the voltages at the points b and c, and the outputs of the comparators 42 and 43 rise from "0" to "1" level respectively. Thus, the monostable multivibrators 52 and 54 generate a pulse so as to supply a set signal to the set terminal S to make the output Q of the flip-flop 60 "1" level, and a gas detection signal of "1" level is supplied to the carburetor 12.

Thus, it is judged that the air-to-fuel ratio is smaller than the set value ST, and the air-to-fuel ratio adjuster in the carburetor 12 works to increase the air-to-fuel ratio of the mixed gas, that is, to lower the density of the mixed gas.

In this way, the air-to-fuel ratio of the mixed gas is adjusted to be the set air-to-fuel ratio ST so that the three dimension catalytic converter 16 purifies $NO_x$, HC and CO with high efficiency.

Next, when the ambient temperature of the gas detection element 21 decreases and the element is used at a working temperature $T_2$, the characteristic of the resistance vs. air-to-fuel ratio becomes as shown by a curve $T_2$ in FIG. 5.

Therefore, the resistance value of the gas detection element 21 changes in a region smaller than the resistance values of the dividing resistors 45A and 46A, thus, the voltages at the points b and c always become smaller than the voltage at the point a, and the voltges at the points b and c do not contribute to discrimination of the air-to-fuel ratio (exhaust gas constituent).

However, the reference voltage at the point d is compared with a voltage responsive to the change of the resistance value of the gas detection element 21, and the reference voltage at the point d contributes to make the air-to-fuel ratio of the mixed gas the set air-to-fuel ratio ST.

Further, when the working temperature of the gas detection element 21 becomes $T_3$ which is in the middle of the working temperature $T_1$ and the maximum working temperature $T_2$, the characteristic of the resistance vs. air-to-fuel ratio of the gas detection element 21 becomes as shown by the curve $T_3$ in FIG. 5.

Therefore, the resistance value of the gas detection element 21 changes in a range smaller than 900 k$\Omega$, so that the reference voltage at the point b becomes always lower than the voltage at the point a, and the reference voltage at the point b does not contribute to discrimination of the air-to-fuel ratio (of an exhaust gas constituent).

Thus, as stated above, the reference voltages at the points c and d are compared with a voltage which changes in response to the exhaust gas constituent, that is, in response to the resistance value change of the gas detection element 21, thereby the reference voltages c and d contribute to making of the air-to-fuel ratio of the mixed gas the set air-to-fuel ratio ST.

In this way, efficient gas detection is secured independently of the working temperature.

The change of the resistance characteristics of a new gas detection element 21 may be sometimes the same as that of the element after the change in lapse of time (after being subjected to a life test). However, in this case also it is possible to carry out a good gas detection in the same way as in the case of temperature change as stated above.

Although in the above embodiment three comparators and three reference voltage generators are used, the number of the comparators and reference voltages may be another plural value. It is needless to say that the value of each resistor may be selected appropriately in accordance with the resistance characteristic of the gas detection element.

The dividing resistors are used for constructing the reference voltage generator, but the reference voltage generator may be of another form, e.g., a voltage generator in which a Zener diode is used.

In the embodiment this invention is applied to an engine using a carburetor, but this invention may be applied also to an engine using a fuel injection means or a secondary air supply means to control a constituent of the exhaust gas flowing into the three-dimension catalyzer as well as an engine using a carburetor. Further, this invention may be applied not only to an engine but also to another system such as a boiler etc. in which a control in response to a constituent of exhaust gas is performed.

What is claimed is:

1. A gas detection apparatus comprising:
   gas detection means for generating a data signal related to a constituent of an exhaust gas;
   a plurality of reference signal generators for generating reference signals which are different from each other;
   a plurality of comparators each having two input terminals, one input terminal of each of said comparators being connected to one of said reference signals, respectively, the other input terminal of all of said comparators being connected to said data signal, each comparator comparing the input signals to generate a comparison signal; and
   logic means for detecting rise and fall of the comparison signals of said plurality of comparators and generating a first gas detection signal when any one of the comparison signals rises, and generating a second gas detection signal when any one of the comparison signals falls.

2. A gas detection apparatus comprising:
   a gas detection element whose electric resistance changes in accordance with a constituent of an exhaust gas;
   a reference resistor connected in series with said gas detection element;
   a plurality of reference voltage generators for generating reference voltages which are different from each other;
   a plurality of comparators each having a non-inverting input terminal and an inverting input terminal, each of one of said inverting and non-inverting input terminals being connected to one of said reference voltages, respectively, the other of said inverting and non-inverting input terminals all being connected to the voltage at a voltage dividing point between said gas detection element and said reference resistor, each comparator comparing the input voltages to generate a comparison signal; and
   logic means for detecting rise and fall of the comparison signals of said plurality of comparators and generating a first gas detection signal when any one of the comparison signals rises, and generating a second gas detection signal when any one of the comparison signals falls.

3. A gas detection apparatus comprising:
   a gas detection element whose electric resistance changes in accordance with a constituent of an exhaust gas;
   a reference resistor connected in series with said gas detection element;
   a plurality of reference voltage generators for generating reference voltages which are different from each other;
   a plurality of comparators each having a non-inverting input terminal and an inverting input terminal, each of one of said inverting and non-inverting input terminals being connected to one of said reference voltages, respectively, the other of said inverting and non-inverting input terminals all being connected to the voltage at a voltage dividing point between said gas detection element and said reference resistor, each comparator comparing the input voltages to generate a comparison signal; and
   a logic circuit for detecting rise and fall of the comparison signals of said plurality of comparators, including a plurality of monostable multivibrators each for generating pulses in response to the rise and fall of a corresponding one of said comparison signals, and a flip-flop for producing a gas detection signal in response to said pulses of said monostable multivibrators.

4. A gas detection apparatus according to claim 3, wherein said monostable multivibrators includes a group of monostable multivibrators each for detecting rise of the comparison signal of one of said comparators, respectively and another group of monostable multivibrators, each for detecting fall of the comparison signal of one of said comparators, respectively, said logic circuit includes two OR gates, output signals from each of the groups of monostable multivibrators being inputted to one of said OR gates, respectively, and said flip-flop has a set terminal and reset terminal, output signals of each of said OR gates being inputted to the set terminal and reset terminal of the flip-flop, respectively.

* * * * *